(12) United States Patent
Anderson

(10) Patent No.: US 6,238,359 B1
(45) Date of Patent: May 29, 2001

(54) CORRECTIVE SHIN SPLINT INSOLE

(75) Inventor: George C. Anderson, Indian Wells, CA (US)

(73) Assignee: Charles A. Smith, Navarre Beach, FL (US)

( * ) Notice: Subject to any disclaimer, the term of this patent is extended or adjusted under 35 U.S.C. 154(b) by 0 days.

(21) Appl. No.: 09/368,407

(22) Filed: Aug. 4, 1999

(51) Int. Cl.[7] .................................................. A61F 5/00
(52) U.S. Cl. ................................... 602/23; 36/43; 36/71
(58) Field of Search ............................ 602/23; 36/28, 36/43, 37, 71, 91, 145

(56) References Cited

U.S. PATENT DOCUMENTS

| | | |
|---|---|---|
| 1,867,431 * | 7/1932 | Wood . |
| 2,190,568 | 2/1940 | Lattemann . |
| 2,623,307 | 12/1952 | Morton . |
| 2,884,719 | 5/1959 | Compton . |
| 3,095,658 | 7/1963 | Midgley . |
| 3,742,627 | 7/1973 | Schneider . |
| 4,180,924 | 1/1980 | Subotnick . |
| 4,317,293 | 3/1982 | Sigle et al. . |

\* cited by examiner

*Primary Examiner*—Michael A. Brown
*Assistant Examiner*—Lalita M Hamilton
(74) *Attorney, Agent, or Firm*—Harry A. Pacini

(57) ABSTRACT

A corrective appliance, as an insole insert, and method of manufacture thereof, an improved insole design of this invention can be used as an insert or sole construction to evert the foot with a raised area having inclined sloping edges at the first metatarsal area with support in the region of the ball of the foot and the first metatarsal head to evert or support the foot by raising the ball of the foot, thereby causing the foot to rotate outwardly, and relieving, reducing and diminishing irritation, inflammation and pain associated with the lower leg ailment commonly known as shin splints.

6 Claims, 2 Drawing Sheets

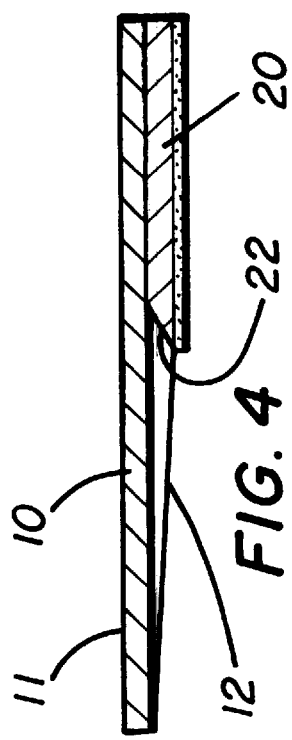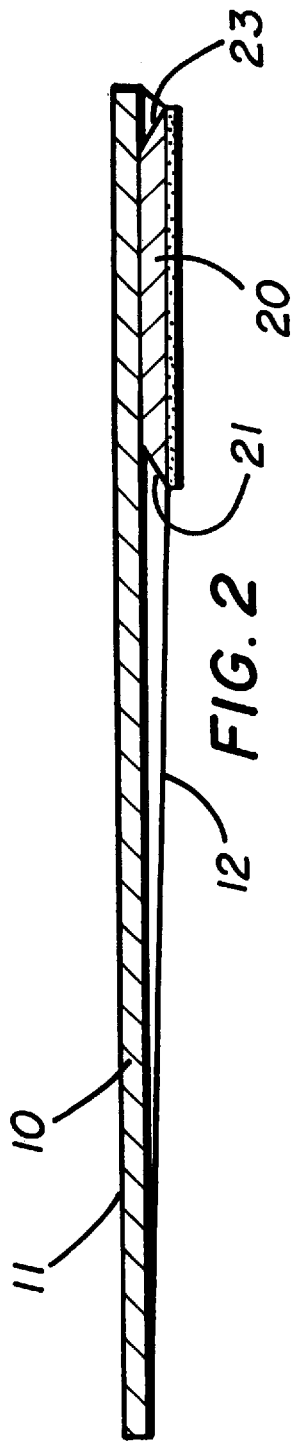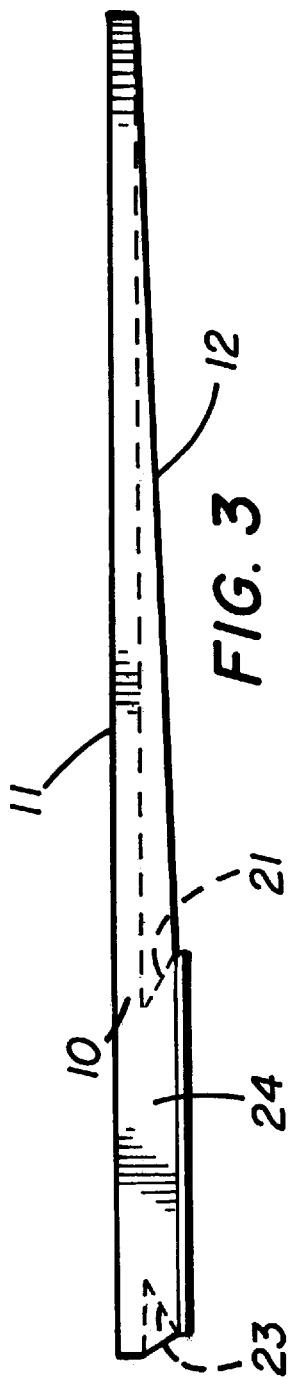

CORRECTIVE SHIN SPLINT INSOLE

BACKGROUND OF THE INVENTION

This invention relates to corrective appliances and more particularly corrective insoles and to the manufacture of corrective insoles or insole inserts constructed to give effective support and relief of the ailment or infirmity known as shin splints.

Shin splints are located in the lower leg on the medial side of the tibia, in the area of the interosseous membrane, which is between the tibia and fibula. Each time the foot makes contact with the ground, the body must absorb a "load." This load is generally the athlete's own body weight. This loading places strenuous demands upon the foot and leg, including the bones in the feet and leg. If measures can be taken to reduce these stresses, then the shoe or an appropriate insole has functioned properly and potential injury can be avoided to the lower leg.

Biomechanics evaluate the demands of a particular injury avoidance. Each activity has its own unique movement, and different stresses on the lower extremities. When running, regardless of the runner's foot fall pattern, the foot is angled slightly inward from the vertical (or "supinated" in biomechanical terms) at touchdown, causing an initial landing on the outside or valgus portion, or lateral aspect, of the heel. Impact results in the foot being rapidly forced on the running surface, causing a bending, or flexion, phase in the knee and hip. Further loading upon initial impact causes the bottom of the foot to be turned away from the body's midline—a phase biomechanics call pronation. The ankle is rolled toward the midline and the whole foot is turned out from the body's midline. This causes the ankle to appear to move in toward the center of the body as the foot lands flat on the ground. After reaching maximum pronation, a propulsion phase begins and all the foregoing actions are reversed.

Pronation or inversion, where the bottom of the foot is turned toward the body's midline is described as abnormal. Pronation during walking and running allows the impact forces to be absorbed over a greater time period. Thus, reducing the effective magnitude of the force without pronation causes excessive stress that would exit on the supporting leg structures. Excessive pronation may be injurious to the walker or runner, and is generally associated with complications of the knee, ankle and lower leg, as in the shin splint. Based on knowledge of the foot function during walking or running, it is desirable to protect the foot and lower leg form excessive forces which will cause injury or irritated membrane in the lower leg.

Since shin splints are located in the lower leg on the medial side of the tibia, when the membrane in the area of the interosseous membrane gets irritated, inflamed and very sore, the condition is known as shin splints. This irritation is common to joggers and walkers as an ailment which comes from running or walking on a hard or uneven surface or sometimes just from walking or running on any surface.

DESCRIPTION OF THE PRIOR ART

The prior art is devoid of a specific corrective appliance, insert of insole which is uniquely useful for correcting the pain or cause of shin splints or interosseous membrane inflammation.

U.S. Pat. No. 4,180,924 discloses a wedged insert which extends from the heel to a point beyond the arch of the wearer's foot and immediately to the rear of the first metatarsal head of the foot. The wedge portion is canted upward its entire length from the outer side of the shoe to the inner side of the shoe. Also, the sole is constructed to be thicker at portions adjacent to the heel than at portions adjacent to the toe.

U.S. Pat. No. 4,317,293 relates to a foot-supporting insole extending from the heel up to a front position of the foot in front of the ball of the little toe at the outside and behind the ball of the big toe on the inside of the foot. Said foot-supporting insole has a substantially constant thickness over its entire area and is curved upwardly at the inside of the foot for support of the arch.

U.S. Pat. No. 3,742,627 relates to an external metatarsal pad for a woman's high heel shoe. The pad is flexible resilient material having a uniform maximum thickness in the rear portion of the pad and gradually tapered at its forward most end. The pad is secured to the outer lower surface of the sole of the shoe.

U.S. Pat. No. 3,095,658 relates to light insoles which are flexible in the forepart, thin but rigid toe area with a strong rear and central shank portion which taper in graduated contours from the full thickness to relatively fine edges at the side. Similarly, U.S. Pat. No. 3,080,589 relates to the method of forming a laminated insole of varying thickness using a multi-ply sheet of a thin layer and a thicker layer of rigid material. An insole blank is cut therefrom leaving a perimeter of rigid material and tapering the thickness of the layer of rigid material in the shank portion from the longitudinal center to the side edges and toward the ball of the foot.

U.S. Pat. No. 2,623,307 describes an orthopedic insole to treat foot and arch disorders in human feet adapted to compensate for shortness or laxity of the metatarsal and a weight-diffusing cushion member and underlying the shafts of all the metatarsal bones from a point immediately back of the heads of all the metatarsals and adapted to diffuse pressure over an area extending laterally across the insole full width.

U.S. Pat. No. 2,190,568 describes an orthopedic shoe or insole with slits extending almost across the entire width of the outer ball portion and an outer wedge tapering from the waist transition to the outer ball. The novel construction of the insole with the slit thin wedge a high degree of flexibility is imparted to the insole and the front portion of the foot is given an inclined position from the outer side toward the inner side.

U.S. Pat. No. 2,884,719 relates to a device, a therapeutic appliance for relief and prevention of metatarsalgia. The device is designed and is used to underlie the great toe and first metatarsal head of the wearer and specifically to relieve the weight load on the second metatarsal head.

DESCRIPTION OF THE INVENTION

It has been found that the improved insole design of this invention can be used as an insert or sole construction to evert the foot with a raised area at the first metatarsal area with support in the region of the ball of the foot and the first metatarsal head. The raised squared portion of the insole is intended to evert or support the foot by raising the ball of the foot, thereby causing the foot to rotate outwardly, and relieving, reducing and diminishing irritation, inflammation and pain associated with the lower leg ailment commonly known as shin splints. The sloped or beveled edges on the front edge and back edge and on the inside edge of the raised portion promotes the desired eversion.

An object of this invention is to provide an insole of a corrective character for shin splints embodying an insole adapted to fit beneath the foot and provide increased eversion and supination of the foot and thereby relieve the ailment known as shin splints.

Another object of this invention is to provide an insole with an improved wedge or insert to the rear of the first metatarsal head of the foot with an upward inclined slopes on the front, back and inside edges of an insole insert to promote eversion of the foot.

Although an insole or pair of insoles would normally form a separate article of commerce from, and be intended for insertion in, a pair of boot or shoes. It also could be integral with such footwear and form a part thereof. It is a further object of the instant invention to provide an insole construction which causes the ball of the foot to be raised and the foot to be rotated outwardly, decreasing pronation and increasing eversion or supination.

Other objects of the invention will be understood and become apparent from the following description and claims, taken in connection with the accompanying drawings.

DESCRIPTION OF THE DRAWINGS

FIG. 2 is a longitudinal sectional taken on line 2—2 of FIG. 1 showing the placement and sloped construction of the raised metatarsal area.

FIG. 3 shows a medial side view along 3—3 of FIG. 1 of the raised metatarsal area.

FIG. 4 is a transverse sectional taken along 4—4 of FIG. 1 showing one sloped side and the non-sloped site.

Referring to the various figures of the drawings wherein like reference characters refer to like parts, there is shown in FIG. 1 one insole constructed in accordance with the instant invention. FIG. 1 designates an insole blank 10 shaped to fit the outline of a shoe last bottom (now shown) to which the insole is usually applied, attached or conforms. If built into a shoe, the insole can be attached into the sole blank in the process of constructing the shoe.

Referring to FIGS. 1, 2, 3 and 4 there is shown in various views a solid insole comprising a foot shaped flattened body having a raised portion supporting the ball of the foot and the first metatarsal head.

Figure 1:
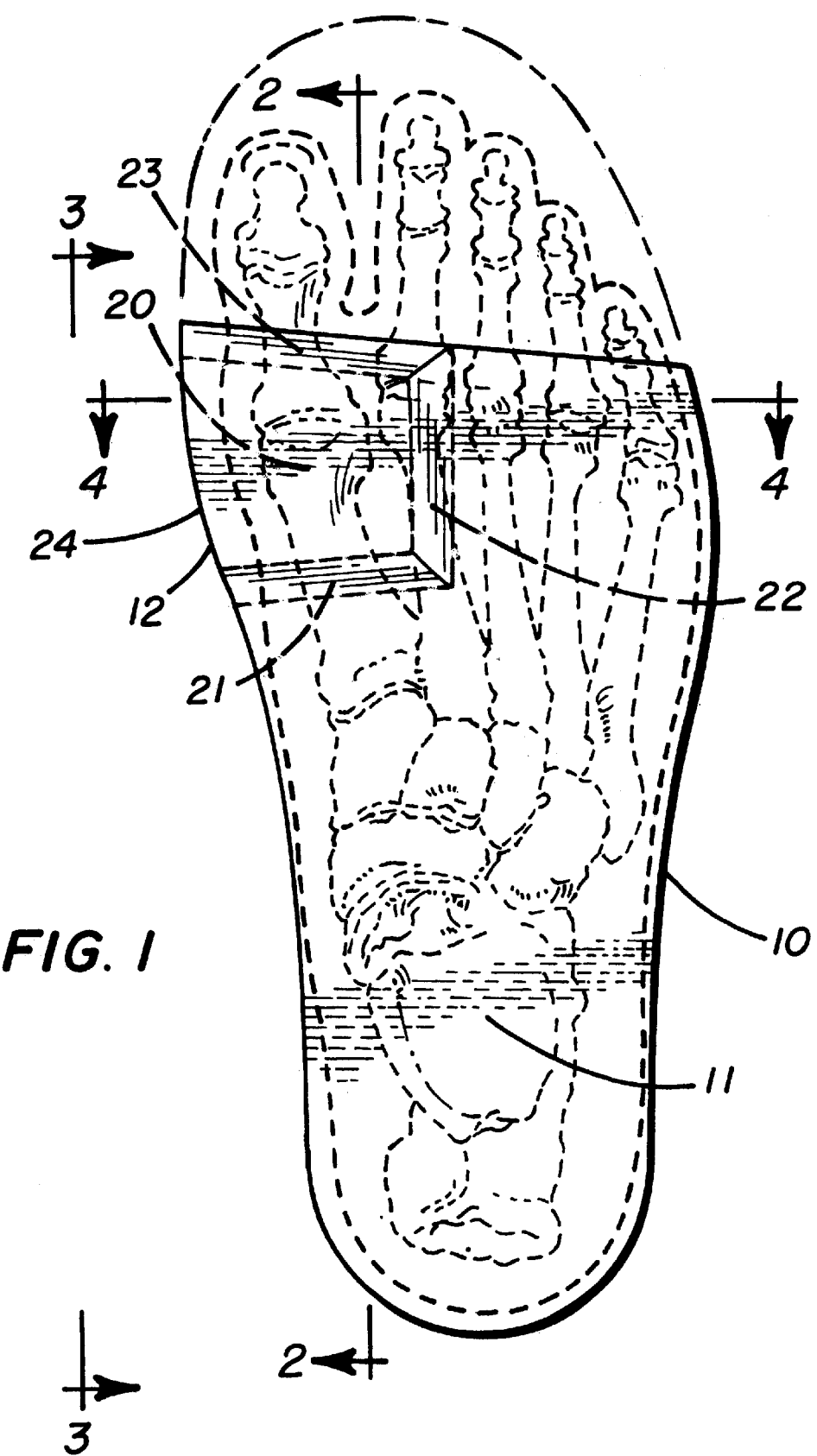
FIG. 1 is a plan view of an insole containing the insert pad.

The shin splint insole is approximately ¾ the length of a shoe inner sole. The material of construction is relatively thin flexible material and for the raised supporting portion of a relatively thicker flexible material, each of which may be chosen, for example, from the list consisting of canvas, duck, nylon or woven plastic material, plastic foam, or a split leather, felt, synthetic leather-rubber composition, or cork-rubber composition, or non-woven cloth. If molded, the entire molded insole is of flexible leather or rubber material. The molded insole is relatively thicker in the lower surface or base 12.

The insole 10 as an entire molded item of flexible material has a raised portion 20 positioned to extend and cover the area representing the base of the big toe (metatarsal) with the metatarsal insert covering the area of the ball of the foot. The insert 10 can be adhesively secured in place to the inner sole of the shoe so as not to move or slip therein.

As represented in the drawings, as an example, the insert is about ⅜ inch thick felt, rubber or combinations thereof, and is beveled, canted or sloped at 21, 22, and 23 as having an upwardly inclined bevel wedge-shape in three directions. By upwardly inclined is meant the slope extends upward from the base 12. The first direction of slope 23 is in the area of the raised edge near the base of the big toe or metatarsal. The second direction slope 22 is at the base of the first metatarsal. The third direction of slope 21 is from the raised insert toward the center of the insole.

As can be seen in FIG. 1, and on section line 2—2 cross-section, the insert is shaped and raised in three directions toward the outside of the shoe as in FIG. 2 and toward the instep at the midsole as in FIG. 1. Note the forward shape of the insert 20 extends along from the midsole to the metatarsal head and from near the outer edge 12 of the insert to the inner sole. FIG. 3 shows a view from the medial side on the insole, showing two sloped sides and a non-sloped side.

In operation when wearing the insert insole, as in a shoe, the raised area slightly lifts the ball of the foot and rotate the foot outwardly which results in relief to the irritated interosseous membrane. The user of the insert is able to continue to jog or walk as the membrane irritation, inflammation and pain diminishes. In the end the pain and irritation is completely relieved.

Also included as an embodiment of this invention is the method of manufacturing an insole insert having a foot shaped configuration and molded of flexible rubber-like material comprising a suitable forming material, which can be the same or different throughout the layer. Said insole insert is preferably a solid one-piece molded flexible rubber-like material coacting with the shaped form. The insole according to the present invention can be made of different materials with appropriate resilient properties. The peripheries of the insole insert are aligned with the inner edge of the insole of the shoe.

Without further elaboration the foregoing will so fully illustrate the invention that its advantages will be apparent to one skilled in the art to which this invention pertains and that various changes may be made in the form, construction and arrangement of the parts without departing form the spirit and scope of the invention or sacrificing its advantages and objectives. The forms herein described and illustrated in the drawings are preferred embodiments thereof.

What is claimed is:

1. A corrective inert insole comprising a major layer approximately the same foot-shape and size as a shoe having an upper surface and a lower surface forming a raised approximate square shaped, insert and having sloped direction in three directions to support the ball of the foot area and the first metatarsal head.

2. The corrective insert sole of claim 1 wherein each of said insole insert is beveled in one direction from the metatarsal region toward the inside middle of the insole and in a second sloped direction from the inside middle of the insole toward an area short of the outer side of the insole and having a third sloped direction forward toward the base of the big toe.

3. A method of manufacturing a shin splint corrective insole insert having an upper surface and a lower surface and a molded flexible material therebetween at the first metatarsal area comprising forming a foot shaped form of resilient flexible material, said form having a raised area at the ball of the foot.

4. The method of claim 3 wherein said material of construction is a flexible rubber-like material of a unitary construction.

5. The method of claim 3 wherein said insole is incorporated into the sole construction of a shoe.

6. The method of claim 3 wherein said materials of construction is of a flexible resilient material.

* * * * *